United States Patent [19]

Becker et al.

[11] 4,198,983
[45] Apr. 22, 1980

[54] CATHETER MADE OF A THERMOPLASTIC MATERIAL HAVING IMPROVED SOFTNESS AND LOW FRICTION

[75] Inventors: Lawrences F. Becker, Chicago; Henry M. Gajewski, Winnetka, both of Ill.

[73] Assignee: Baxter Travenol Laboratories, Inc., Deerfield, Ill.

[21] Appl. No.: 900,965

[22] Filed: Apr. 28, 1978

[51] Int. Cl.² .................. A61M 25/00; C08L 43/04
[52] U.S. Cl. .................................. 128/349 R; 525/95
[58] Field of Search .................. 260/827; 128/214 R, 128/348, 349

[56] References Cited
U.S. PATENT DOCUMENTS

| | | | |
|---|---|---|---|
| 3,691,257 | 9/1972 | Kendrick et al. | 260/827 |
| 3,932,555 | 1/1976 | Goodrich et al. | 260/827 X |
| 4,154,244 | 5/1979 | Becker et al. | 128/349 B |

OTHER PUBLICATIONS

"Fatty Acids" *Encyclopedia of Chem. Tech.*, Kirk & Othmer, Ed. 2, Wiley, 1965, pp. 842 & 845.

*Primary Examiner*—Robert W. Michell
*Assistant Examiner*—Thomas Wallen
*Attorney, Agent, or Firm*—Paul C. Flattery; John P. Kirby, Jr.; Garrettson Ellis

[57] ABSTRACT

A catheter, preferably a balloon-type catheter, is disclosed in which the catheter shaft is made of a thermoplastic material and thus may be extrudable, the shaft consisting essentially of (a) from 40 to 70 percent by weight of an elastic composition which comprises: from 50 to 99.5 percent by weight of a block copolymer having thermoplastic rubber characteristics with a central, rubbery polyolefin block and terminal blocks of polystyrene, and optionally including up to about 45 percent by weight of polypropylene, plus from 0.5 to 10 percent by weight of a cross-linked organic silicone elastomer; and (b) from 30 to 60 percent by weight of a hydrophobic oil-type plasticizer to provide the desired degree of softness to said elastic composition.

13 Claims, 2 Drawing Figures

CATHETER MADE OF A THERMOPLASTIC MATERIAL HAVING IMPROVED SOFTNESS AND LOW FRICTION

BACKGROUND OF THE INVENTION

Balloon catheters are commonly used in urinary tract surgery. For example, the Foley catheter is the most common balloon type catheter, being inserted into the urethra until the catheter extends into the bladder. Then, a balloon adjacent the head is inflated to retain the catheter for usually a period of days, although catheters may need to be implanted for a longer period of time in certain situations.

Other catheters, with and without balloons, are used for gastric and other purposes.

The early designs of Foley catheters were generally made of natural rubber latex. As is known, the latex can cause a reaction in the tissues which are adjacent to it. This can be very uncomfortable for the patient, and it is, of course, undesirable from a medical viewpoint.

Some catheters have been fabricated out of silicone rubber, or out of latex which is coated with a film of silicone rubber, to avoid the tissue reaction problem. Such catheters are, however, more expensive than latex catheters, and they are also somewhat difficult to fabricate, as are latex catheters, because both of the above materials are generally not thermoplastic materials, but must be cured over a period of time to obtain the desired physical properties.

Another type of balloon catheter has a polyvinyl chloride tubular shank attached to a natural rubber latex balloon, since vinyl is unsuitable as a balloon material. Thus, the latex balloon remains as an irritant, and vinyl catheters have exhibited an undesirable "feel" to the patient.

In U.S. patent application Ser. No. 853,738, filed Nov. 21, 1977 now U.S. Pat. No. 4,154,244, a catheter which comprises an oil-filled, thermoplastic rubber material is shown which exhibits a very low toxicity so that little or no irritation is felt by the patient, and which has other advantages as well.

This present invention constitutes an improvement upon the invention of the prior art patent application in that the surface of the catheter of this invention exhibits a substantially reduced friction to the body and the like, and also exhibits a significantly reduced tendency to collect encrustation, the surface exhibiting a high degree of smoothness and gloss.

The balloon of the catheter of this invention exhibits particularly good elastomeric recovery, with low creep, so that there is little "pruning" upon deflation of the balloon, i.e. the formation of wrinkles in the balloon.

While the material of the catheter of this invention, on a cost basis, is similar to natural rubber latex and the like, it is as non-toxic as silicone rubber, thereby combining the advantages of the two types of catheters.

Also, as a further advantage, the tubular shaft of the catheter of this invention may be formed by simple extrusion, without a post cure time, since the material of the catheter may be thermoplastic, but also of a softening temperature which permits autoclaving of the catheter if desired.

Also, parts of the catheter may be thermoformed or injection molded as desired. The tubing of the catheter of this invention may be kink and collapse resistant upon aspiration and normal use, and it may be fabricated by heat sealing, without separate adhesives.

Also, the cost of fabrication of the catheters of this invention may be further reduced by the fact that scrap materials from the production of the catheter may be reused in molding or extrusion, since the material is of thermoplastic rather than of the thermoset type.

The catheters of this invention are also stable under radiation sterilization.

DESCRIPTION OF THE INVENTION

In accordance with this invention, a catheter is provided, preferably a balloon-type catheter, which comprises a tubular shaft and, in the case of balloon-type catheters, an inflatable balloon member carried by the catheter. The shaft consists essentially of (a) from 40 to 70 percent by weight of an elastic composition which comprises:

from 50 to 99.5 percent by weight of a block copolymer having thermoplastic rubber characteristics with a central rubbery polyolefin block and terminal blocks of a polystyrene. The block copolymer preferably exhibits a Brookfield viscosity at 25° C. at 10 to 2000 cps., when measured using a 10 percent by weight solids solution in toluene. The composition also may contain up to 45 percent by weight of polypropylene, and from 0.5 to 10 percent by weight of a cross-linked silicone elastomer, preferably of the type described below, and preferably no more than 5 percent.

Added to this is preferably 30 to 60 percent by weight of a hydrophobic oil-type plasticizer to provide the desired degree of softness to said elastic composition. In the case of balloon-type catheters, the balloon member is sealed in its position on the shaft.

Preferably, the cross-linked silicone elastomer is the reaction product of (a) an organopolysiloxane, preferably a dimethylpolysiloxane, containing from 1 to 5 percent by weight of siloxane units which contain silicon-bonded vinyl groups, and (b) a preferably generally stoichiometric amount of an organopolysiloxane material, preferably a methylsiloxane, containing silicon-bonded hydrogen. It has been found that this material, which crosslinks in the presence of a platinum-type catalyst in a well-known manner, provides particularly satisfactory surface characteristics in the formulation, unlike other cure systems for silicones.

Without wishing to be limited or bound by any theory of operation, it is believed that an inhibitory effect is present in the type of formulation used in this invention which interferes with the curing of silicones of different type cure systems. The organic silicone elastomers which are preferred for use in this invention are believed to cure by the reaction of silicon-bonded vinyl groups with silicon-bonded hydrogen groups to create a crosslinked structure, and silicone formulations utilizing this type of cure system are commercially available.

The silicone crosslinked structure in the formulation of this invention can also be used to improve the resilience and tensile set of the resulting product, and to reduce encrustation of the catheter in use, among other properties.

Preferably, the elastic composition as defined above is present in the catheter formulation in a concentration of 55 to 65 percent by weight, while the oil-type plasticizer is present in the concentration of 35 to 45 percent by weight, to obtain the most desirable levels of softness for use as a medical catheter.

It has also been found to be desirable in certain circumstances to include in the elastic composition from about 0.5 to 3 percent by weight of a fatty acid amide having an average of about 16 to 50 carbon atoms per molecule, whereby the combination of the cured silicone elastomer and the fatty acid amide ingredient provides the catheter with a surprisingly and substantially reduced surface friction above and beyond that which is normally contributed by either of the ingredients alone. For example an amide of erucic acid, or the diamide N,N'ethylene-bisstearamide, may be used. P The organic silicone elastomer is preferably based upon a dimethylsiloxane gum, but other silicon-bonded organic units may also be present to provide phenylmethyl, diphenyl, ethylmethyl, and 3,3,3-trifluoropropylmethyl siloxane units, and the like.

The block copolymers having thermoplastic rubber characteristics as described above are commercially available under the trademark KRATON from the Shell Chemical Company or SOLPRENE from the Phillips Petroleum Company. The rubbery polyolefin block utilized herein is preferably poly(ethylene-butylene), particularly those copolymers with approximately equal amounts of the respective two copolymer units. However, other useful commercially available materials have a central, rubbery polyolefin block of butadiene or isoprene, and may be used in this invention.

The rigid, usually terminal blocks of the block copolymer having thermoplastic rubber characteristics customarily consist of polystyrene, although it is contemplated that derivatives of polystyrene and other equivalent materials can be used as well.

Mixtures of the above described block copolymers of differing molecular weight may also be desirable for use. An advantage of such mixtures is that a component of the mixture may include the block copolymer as described above with a molecular weight which is in itself too high to permit extrusion, with the extrudability being facilitated by a component of lower molecular weight block copolymer, to obtain an advantage in physical properties from the high molecular weight component (for example, a solution viscosity as calculated above of 1000 cps.). The lower molecular weight components of the block copolymer described above may preferably have similar solution viscosities on the order of 20 to 100 cps.

Preferably, in the block copolymers described above, the central block of ethylene-butylene units may comprise 50 to 85 percent by weight of the copolymer molecule, while the terminal blocks of polystyrene or equivalent material comprise the balance of the compound.

This formulation used herein may also contain a titanium dioxide pigment or the like, for appropriate coloration of the catheter, as well as other desired additives such as stabilizing agents, plasticizers such as mineral oil, and flow aid and hardener materials such as polypropylene.

Typically, a molded, branched connector such as a Y-site is attached at the distal end of the tubular shaft of the catheter. The branched connector may also be made of the elastic composition described above.

Either or both of the shaft and the balloon member (and the branched connector when used) desirably may contain from 5 to 30 percent by weight of tackifying agent such as low molecular weight polystyrene. When at least one of the formulations contains this material, it facilitates the adhesion of the balloon member and the Y-connector to the catheter shaft without the use of adhesive by heat sealing or molding the balloon member and connector in place on the shaft. The polystyrene material used may preferably be of a molecular weight, for example, of 1000 to 6000.

Preferably up to 30 percent of the polypropylene may be used in the oil-extended compound, both as a flow aid and as a surface finish, depending on the molecular weight of the polypropylene. Generally, more polypropylene is needed as a flow or extrusion aid when the block copolymers used in this invention are of higher molecular weight. In particular, from about one to ten weight percent of polypropylene having a melt flow of about 50 to 100, as tested under ASTM D1238-70, provides an improved, smooth surface finish. Also, crystalline polypropylene is believed to act as a diffusion barrier.

Figure 1:
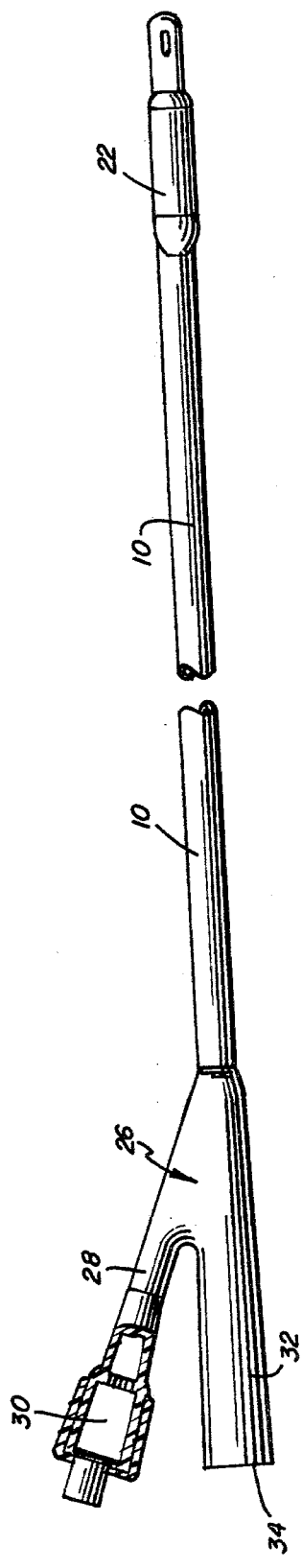
FIG. 1 is a plan view of a typical Foley catheter which may be manufactured in accordance with this invention.
Figure 2:
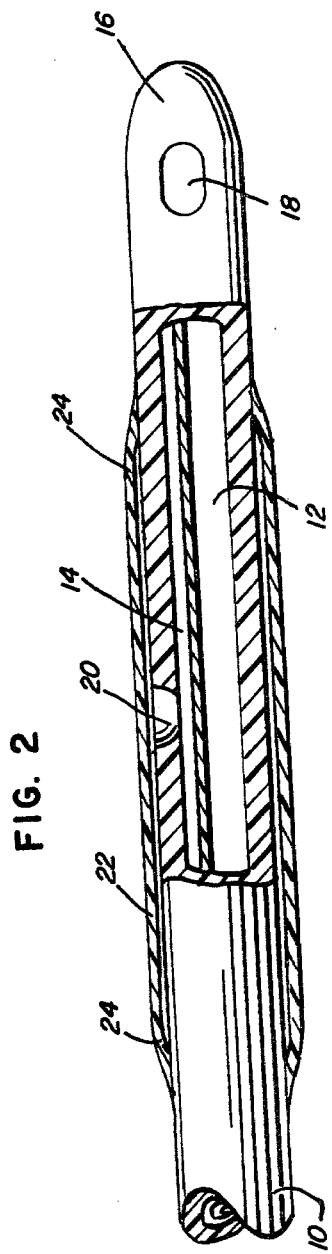
FIG. 2 is a detailed view of the catheter of FIG. 1, taken partly in section, showing the catheter balloon member adhered to the catheter shaft.

Referring to the drawings, the catheter of this invention is shown defining a double lumen tubular shaft 10 which may be extruded to define a drainage lumen 12 and an inflation lumen 14 in accordance with conventional technology. Tip member 16 may be conventionally thermoformed on the catheter so that drainage lumen 12 communicates through aperture 18 to the exterior, and inflation lumen 14 is closed off.

Aperture 20 is provided in the wall of shaft 10 to provide communication between the inflation lumen 14 and the exterior of shaft 10. Balloon 22, being a thin-walled tube, for example may be bonded by a non-contact radiant heat source, at ends 24 to the outer wall of shaft 10 about aperture 20. Accordingly, when pressurized air or liquid is provided to inflate lumen 14, balloon 22 will expand.

Branched or Y-connector 26 comprises a pair of branching channels. Channel 28 is adapted to receive a pressure syringe, and communicates with the inflation lumen 14. Valve 30 is provided to receive the luer of a syringe and to allow it to pass to place pressurized fluid into the inflation lumen 14. Valve 30 is also adapted to retain that pressure when the syringe is withdrawn, and may be of conventional construction for a Foley catheter. Branched tube 32 is adapted to communicate with the catheter adapter of a urinary drainage bag or the like at its outer end 34, and communicates with drainage lumen 12 within catheter shaft 10.

The following examples are provided to illustrate specific examples of formulations which may be utilized in the catheter of this invention. These specific examples are for illustrative purposes only, and are not intended to limit the scope of the invention of this application, which is as defined in claims below.

EXAMPLE 1

A material for formulating extruded shaft 10 of the catheter of this invention was prepared by mixing the following ingredients in a Welex dry blender from the Welex Inc. of King of Prussia, Pa.: 30 parts by weight of a formulation (KRATON G1652) of a block copolymer of poly(ethylene-butylene) with polystyrene end blocks, in which the poly(ethylene-butylene) portion of the copolymer comprises about 70 percent by weight of a copolymer molecule, having a Brookfield viscosity at 25° C. of 20 cps., using a 10 weight percent solution in toluene, and containing from 0.03 to 0.07 of an equal weight mixture of two stabilizers, one commercially available under the trademark IRGANOX 1010 by the Ciba-Geigy Company, and the other being dilaurylthiodipropionate. Alternatively, the antioxidant may be AO330 antioxidant, sold by the Ethyl Corporation.

To this was added 20 parts by weight of a block copolymer (KRATON G1650) having thermoplastic rubber characteristics with a central copolymer block of poly(ethylene-butylene) in generally equimolar proportions, and terminal blocks of polystyrene, the material having a Brookfield viscosity of 60 cps. using a 10 weight percent solution in toluene, 25° C. The poly(ethylene-butylene) portion of the copolymer comprises about 70 percent by weight of the copolymer molecule.

To 42 parts by weight of USP light grade white mineral oil, manufactured by Witco Chemical Company, Sonneborn Division, New York, New York called KAYDOL (viscosity at 100° F. of 350 Saybolt seconds) was added one half part by weight each of a two-component methylpolysiloxane elastomer. The methylpolysiloxane elastomer comprises a first component of dimethylpolysiloxane, containing from one to five percent by weight of siloxane units which contain silicon-bonded vinyl groups, and a generally stoichiometric amount of a methyl polysiloxane material containing silicon-bonded hydrogen, with a platinum-type catalyst included (Dow Corning Q39590A and Q39590B).

There was then also added two parts by weight of a polypropylene having a melt flow of approximately 2, according to ASTM D-1238 (Condition L) and 5 parts by weight of a high melting polypropylene (TENITE 4G7DP, sold by Eastman Chemical Products, Inc.) having a melt flow of 60, according to ASTM D1238-70, as a surface finish improving agent.

The polymer materials were mixed at low r.p.m. in the Welex dry blender, and the mixture of the mineral oil and silicone formulation was added. The blender speed was raised to a high r.p.m., and allowed to operate until the temperature of the contents rose to 110° F. Then the blender speed was reduced to low r.p.m. again. The resulting material was then put into a ribbon blender and chilled to room temperature.

To 100 parts by weight of the above mixture, 2 parts of titanium oxide pigment (Ti-Pure R221) was mixed in. The material was then pelletized and extruded at a die temperature of 375° F. to form catheter shaft 10. The same material was used to mold branch connector 26 on shaft 10, and tip member 16 was conventionally thermoformed on the catheter in the manner described above, and eyelets 18 were punched.

The resulting catheter shaft exhibited substantially increased slippery characteristics over the silicone-free material, and exhibited improved surface finish and reduced tendency for attachment of encrustation.

The balloon material was extruded in conventional manner out of a formulation containing the following ingredients:

(a) 55 percent by weight of a mixture of 100 parts by weight of a block copolymer of poly(ethylene-butylene) having terminal blocks of polystyrene (known as KRATON G1651-Brookfield viscosity at a 10 weight percent solution in toluene at 25° C.: 1000 cps.: weight percent of the central block: 67 percent) and 85 parts by weight of the KAYDOL mineral oil described above.

(b) 25 percent by weight of the KRATON G1650 block copolymer described above, and (c) 20 percent by weight of the KAYDOL mineral oil described above.

To 100 parts by weight of the above mixture was added two parts of the titanium oxide pigment described above, and one part of an amide of erucic acid (KEMAMIDE E) for reducing surface friction. This material was extruded at a die temperature of 450° F. to form the balloon members, which were then sealed onto the catheter shaft prepared above to provide an improved Foley catheter.

EXAMPLE 2

Foley catheters in accordance with Example 1 were prepared, with the exception that the formulation for the catheter shaft was reduced to 41 percent of the KAYDOL mineral oil, and one percent of each component of the curable methylpolysiloxane formulation was added. Furthermore, there was added to the shaft formulation, along with the two parts by weight of titanium dioxide, one part by weight of the fatty acid amide (KEMAMIDE E) for reducing the surface friction.

The resulting catheter shaft exhibited significantly reduced frictional characteristics, even when compared with the excellent frictional characteristics of the catheter of Example 1, and also showed significant improvement over a catheter shaft formulation similar to that of Example 1, except for containing 43 percent by weight of the KAYDOL mineral oil, no silicone ingredient, and an added one part of the same fatty acid amide with the two parts of the titanium oxide pigment added.

That which is claimed is:

1. A catheter which comprises a tubular shaft, said shaft consisting essentially of (a) from 40 to 70 percent by weight of an elastic composition which comprises: from 50 to 99.5 percent by weight of a block copolymer having thermoplastic rubber characteristics with a central rubbery polyolefin block and terminal blocks of a polystyrene; said block copolymer exhibiting a Brookfield viscosity at 25° C. of 10 to 2000 cps., when measured using a 10 percent by weight solids solution in toluene, said composition including from 0 to 45 percent by weight of polypropylene, and from 0.5 to 10 percent by weight of a crosslinked, organic silicone elastomer which is the reaction product of an organopolysiloxane containing from one to five percent by weight of siloxane units which contain silicon-bonded vinyl groups, and an organopolysiloxane material containing silicon-bonded hydrogen; and (b) from 30 to 60 percent by weight of a hydrophobic oil-type plasticizer to provide the desired degree of softness to said elastic composition.

2. The catheter of claim 1 in which said shaft consists essentially of 55 to 65 percent by weight of said elastic composition and 35 to 45 percent by weight of said hydrophobic oil-type plasticizer.

3. The catheter of claim 1, in which said elastic composition also includes from 0.5 to 3 percent by weight of a fatty acid amide having an average of 16 to 50 carbon atoms per molecule, whereby the combination of the cured silicone elastomer and fatty acid amide ingredient provides the catheter with substantially reduced surface friction.

4. The catheter of claim 1 in which said organic silicone elastomer is the reaction product of a dimethylpolysiloxane containing from 1 to 5 percent by weight of siloxane units which contain silicon-bonded vinyl groups, and a methylpolysiloxane material containing silicon-bonded hydrogen.

5. The catheter of claim 1 in which the formulation for said shaft contains from 1 to 10 percent by weight of polypropylene having a melt flow of essentially 50 to 100, as tested under ASTM D1238-70.

6. The catheter of claim 1 which carries an inflatable balloon member sealed on said shaft.

7. The balloon-type catheter of claim 6 in which said block copolymer of the shaft and balloon member has a central, rubbery polyolefin block of poly(ethylene-butylene).

8. A plastic formulation which comprises (a) from 50 to 70 percent by weight of an elastic combination which comprises: 50 to 99.5 percent by weight of a block copolymer having thermoplastic rubbery characteristics with a central rubbery polyolefin block and terminal blocks of a polystyrene; said block copolymer exhibiting a Brookfield viscosity at 25° C. of 10 to 2000 cps. when measured using a 10 percent by weight solids solution in toluene, said composition including from 0 to 45 percent by weight of polypropylene, and from 0.5 to 5 percent by weight of a crosslinked organic silicone elastomer which is the reaction product of an organopolysiloxane containing from one to five percent by weight of siloxane units which contain silicon-bonded vinyl groups, and a methyl polysiloxane material containing silicon-bonded hydrogen; and (b) from 30 to 50 percent by weight of a hydrophobic oil-type plasticizer to provide the desired degree of softness to said elastic composition.

9. The composition of claim 8 in which from 55 to 65 percent by weight of said elastic composition and 35 to 45 percent by weight of said hydrophobic oil-type plasticizer are present.

10. The composition of claim 8 which also includes from 0.5 to 3 percent by weight of a fatty acid amide having an average of 16 to 50 carbon atoms per molecule, whereby the combination of the cured silicone elastomer and fatty acid amide ingredient provides the catheter with substantially reduced surface friction.

11. The composition of claim 8 in which said organic silicone elastomer is the reaction product of a dimethylpolysiloxane containing from 1 to 5 percent by weight of siloxane units which contain silicon-bonded vinyl groups, and a methylpolysiloxane material containing silicon-bonded hydrogen.

12. The catheter of claim 8 in which said composition contains from 1 to 10 percent by weight of polypropylene having a melt flow of essentially 50 to 100 as tested under ASTM D1238-70.

13. The composition of claim 8 in which said block copolymer has a central, rubbery polyolefin block of poly(ethylene-butylene).

* * * * *